United States Patent
Seifi

(10) Patent No.: US 12,076,484 B2
(45) Date of Patent: Sep. 3, 2024

(54) HICCUP RELIEVING APPARATUS

(71) Applicant: The Board of Regents of the University of Texas System, Austin, TX (US)

(72) Inventor: Ali Seifi, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 403 days.

(21) Appl. No.: 16/802,432

(22) Filed: Feb. 26, 2020

(65) Prior Publication Data

US 2020/0188619 A1     Jun. 18, 2020

Related U.S. Application Data

(63) Continuation-in-part of application No. PCT/US2019/013728, filed on Jan. 16, 2019.
(Continued)

(51) Int. Cl.
*A61M 16/04*     (2006.01)
*A47G 21/18*     (2006.01)
(Continued)

(52) U.S. Cl.
CPC ........... *A61M 16/049* (2014.02); *A47G 21/18* (2013.01); *A61M 16/0003* (2014.02);
(Continued)

(58) Field of Classification Search
CPC ... A47G 21/18; A61J 7/0038; A61M 16/0003; A61M 16/049; A61M 2205/076;
(Continued)

(56) References Cited

U.S. PATENT DOCUMENTS 3,236,100 A     5/1861   Hall
1,314,374 A     8/1919   Stair
(Continued)

FOREIGN PATENT DOCUMENTS

CN    B03132216 S    7/2014
CN    304101131 S    12/2016
(Continued)

OTHER PUBLICATIONS

"Hiccaway, the Only Drug Free Solution Guaranteed to Get Rid of Hiccups" by Hiccaway Information. Youtube. Posting date: Mar. 11, 2020. Retrieval date: Jun. 27, 2022. Retrieved from internet: https://www.youtube.com/watch?v=u6_s6WD8PbE (Year: 2020).
(Continued)

*Primary Examiner* — Colin W Stuart
*Assistant Examiner* — Matthew D Ziegler
(74) *Attorney, Agent, or Firm* — Neugeboren O'Dowd PC

(57) ABSTRACT

The hiccup relieving apparatus includes a body with a first end having a mouthpiece, a second end having a restriction in the body between the first end and the second end. The restriction makes it difficult to draw fluid through the body to the user's mouth. The fluid can be air or the body can be immersed in water or other potable liquid in a container. The restriction requires an adult user, using the mouthpiece, to produce a threshold suction of for example water before water can flow from the water in the water container, through the body, through the mouthpiece, and to the user.

19 Claims, 5 Drawing Sheets

Related U.S. Application Data

(60) Provisional application No. 62/619,196, filed on Jan. 19, 2018.

(51) Int. Cl.
   *A61J 7/00* (2006.01)
   *A61M 16/00* (2006.01)

(52) U.S. Cl.
   CPC ....... *A61J 7/0038* (2013.01); *A61M 2205/076* (2013.01); *A61M 2205/3331* (2013.01); *A61M 2210/0656* (2013.01); *A61M 2210/1014* (2013.01); *A61M 2210/1039* (2013.01)

(58) Field of Classification Search
   CPC .. A61M 2205/3331; A61M 2210/0656; A61M 2210/1014; A61M 2210/1039
   See application file for complete search history.

(56) References Cited

U.S. PATENT DOCUMENTS

| | | | |
|---|---|---|---|
| 2,488,988 A | | 11/1949 | Schmitt |
| 2,812,257 A | | 11/1957 | Scisorek |
| 2,943,794 A | | 7/1960 | Sussman |
| 3,610,483 A | * | 10/1971 | Visconti ............... A61J 7/0046 215/11.5 |
| 3,721,240 A | * | 3/1973 | Tamburri ............. A61M 15/06 128/202.21 |
| 4,150,071 A | | 4/1979 | Pecina |
| 5,094,861 A | | 3/1992 | D'Auguste et al. |
| 5,156,335 A | | 10/1992 | Smith |
| 5,234,117 A | * | 8/1993 | Garvin ................. A47G 21/18 215/11.4 |
| 5,509,605 A | | 4/1996 | Cripe |
| 5,518,613 A | | 5/1996 | Koczur |
| 5,899,201 A | * | 5/1999 | Schultz ............... A61M 11/002 128/200.14 |
| 5,910,321 A | | 6/1999 | Wong et al. |
| 5,985,324 A | | 11/1999 | Wong et al. |
| D433,502 S | | 11/2000 | Rand |
| 6,145,503 A | | 11/2000 | Smith |
| D441,859 S | | 5/2001 | Pera |
| 6,341,605 B1 | * | 1/2002 | Ohki .................. A61M 15/002 128/203.15 |
| 6,550,493 B2 | * | 4/2003 | Williamson ......... A47G 21/185 137/907 |
| D497,666 S | | 10/2004 | Lien |
| 7,089,934 B2 | * | 8/2006 | Staniforth ............ A61K 9/145 128/203.15 |
| D564,278 S | | 3/2008 | Villalobos |
| 7,584,900 B2 | | 9/2009 | White et al. |
| D629,508 S | | 12/2010 | Zuyderhoudt |
| 8,127,789 B2 | * | 3/2012 | Schafer .................. F16K 15/04 239/24 |
| 8,376,246 B2 | * | 2/2013 | White ................. A47G 21/182 239/16 |
| D681,804 S | | 5/2013 | Sheehy |
| D692,140 S | | 10/2013 | Alvino |
| 8,931,634 B2 | | 1/2015 | Anderson |
| D732,870 S | | 6/2015 | Hollander et al. |
| 9,167,928 B2 | * | 10/2015 | Hanners ................. A47G 21/18 |
| D775,347 S | | 12/2016 | Buess |
| 10,307,005 B1 | * | 6/2019 | Pierce ................. A47G 21/188 |
| D933,409 S | | 10/2021 | Serrahima et al. |
| D933,812 S | | 10/2021 | Lary |
| 11,259,659 B2 | * | 3/2022 | Zonnenberg ........... A47G 21/18 |
| 2004/0112826 A1 | | 6/2004 | Chiba |
| 2005/0080458 A1 | | 4/2005 | Ehlinger |
| 2006/0192025 A1 | | 8/2006 | White |
| 2009/0314736 A1 | | 12/2009 | Rigert |
| 2010/0155500 A1 | | 6/2010 | Zaccheo |
| 2014/0190473 A1 | | 7/2014 | Haindl |
| 2020/0188619 A1 | | 6/2020 | Seifi |

FOREIGN PATENT DOCUMENTS

| | | | | |
|---|---|---|---|---|
| CN | 305431335 S | | 3/2019 | |
| CN | 306246910 S | | 7/2020 | |
| CN | 306727662 S | | 4/2021 | |
| CN | 306758018 S | | 4/2021 | |
| CN | 306938434 S | | 7/2021 | |
| EP | 3871566 B1 | | 9/2021 | |
| GB | 2412876 | | 10/2005 | |
| GB | 2412876 A | * | 10/2005 | .......... A61M 15/002 |
| TW | D191936 S | | 11/2017 | |
| WO | 2019143643 A1 | | 7/2019 | |

OTHER PUBLICATIONS

Hiccaway: The Original Natural Remedy Proven to Stop Hiccups Instantly by HiccAway. Amazon. Date first available: Aug. 7, 2020. Retrieval date: Jun. 27, 2022. Retrieved from internet: https://www.amazon.com/Hiccaway-Hiccup-Relief-Hiccups-Treatment/dp/B08C1Y3GRC (Year: 2020).

Instagram post by Hiccaway, "Introducing Hiccaway, the only solution you'll ever need to get rid of those pesky Hiccups!" Instagram posting date: Mar. 17, 2020. Retrieval date: Jun. 29, 2022. Retrieved from internet: https://www.instagram.com/p/B90prZbJXwX (Year: 2020).

Counterpart Canadian Patent Application No. 3086723, Requisition by Examiner dated Feb. 19, 2024. 3 pages.

Counterpart Canadian Patent Application No. 3086723, Requisition by Examiner dated Mar. 6, 2024. 3 pages.

Counterpart European Patent Application No. 20191264.3, Extended European Search Report dated Feb. 1, 2021. 10 Pages.

Counterpart European Patent Application No. 20191264.9. Communication under Rule 71(3) EPC. 6 pages. Dated Jul. 26, 2023.

Counterpart Patent Application No. 19741354.5, Communication pursuant to Artle 94(3) EPC dated Mar. 5, 2024. 4 pages.

U.S. Appl. No. 16/963,240, filed Jul. 19, 2020. Office Action dated Jun. 29, 2023. 19 pages.

U.S. Appl. No. 16/963,240, filed Jul. 19, 2020. First named inventor: Seifi. Final office action dated Apr. 2, 2024. 53 pages.

* cited by examiner

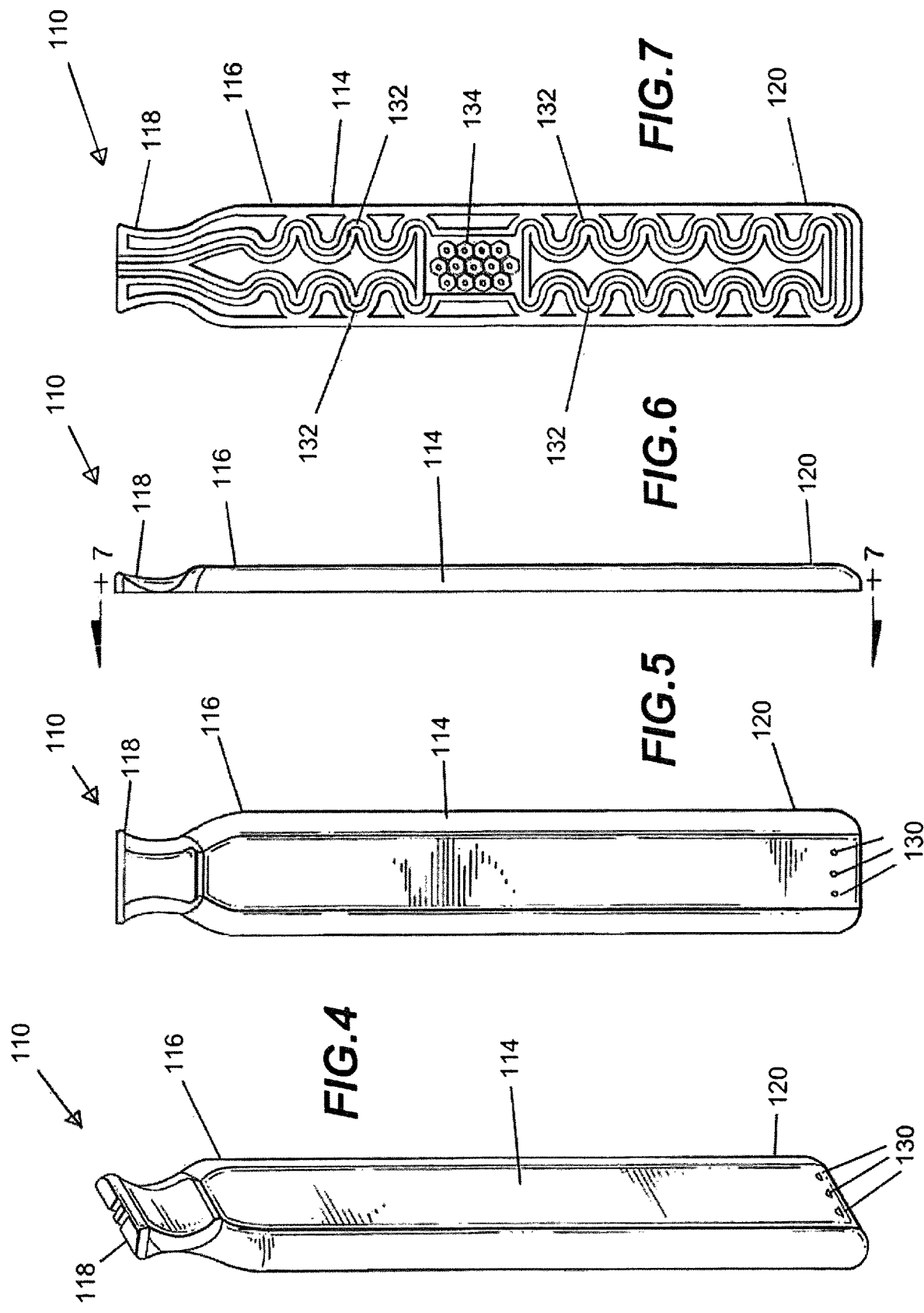

HICCUP RELIEVING APPARATUS

CROSS REFERENCE TO RELATED APPLICATION

This application is a continuation-in-part of PCT Patent Application Ser. No. PCT/US2019/013728, filed on Jan. 16, 2019, which claims priority to U.S. Provisional Application No. 62/619,196, filed on Jan. 19, 2018, the entire disclosures of which are incorporated herein by reference in their entireties.

FIELD OF THE INVENTION

This invention relates to an apparatus for alleviating hiccups.

BACKGROUND OF THE INVENTION

A hiccup is an involuntary spasm of the diaphragm muscle resulting in an involuntary inhalation that is abruptly interrupted by the involuntary closing of the glottis and resulting in the familiar and characteristic sound of a hiccup. The exact anatomic and physiological mechanism responsible for causing hiccups remains unknown. Currently, there are several simple cures that involve Vagal nerve stimulation and can include drinking a glass of water rapidly, swallowing dry bread or crushed ice, inducing vomiting, applying traction on the tongue, or applying pressure on the eyeballs.

SUMMARY OF THE INVENTION

The hiccup relieving apparatus of the present invention addresses the need for a simple device for facilitating a cure for hiccups. The present invention is simple, inexpensive to construct, and easy to use. The hiccup relieving apparatus comprises a tube with a first end having a mouthpiece, a second end that can be immersed in water or other potable liquid, and a restriction that causes a pressure differential between the first end and the second end of the tube. The restriction requires the user, using the mouthpiece, to produce a threshold suction between 10 and 40 cm of water, before fluid, such as water, can flow from the container, through the tube, through the mouthpiece, and to the user. The ideal pressure differential depends on body mass and lung capacity; however, we have found the range of 20 to 30 cm of water to be most suitable for a wide target population. The restriction can take the form of a restricting orifice in the second end of the tube, a threshold valve in the tube, a wad of cotton in the tube, a wad of other cellulosic material in the tube, or restricting orifices adjacent the second end of the tube in combination with serpentine channels extending from the orifices to the mouthpiece.

Further objects, features and advantages will become apparent upon consideration of the following detailed description of the invention when taken in conjunction with the drawings and the appended claims.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 4 is a perspective view of a third embodiment of the hiccup relieving apparatus in accordance with the present invention.

FIG. 5 is a front elevation view of the third embodiment of the hiccup relieving apparatus in accordance with the present invention.

FIG. 6 is a side elevation view of the third embodiment of the hiccup relieving apparatus in accordance with the present invention.

FIG. 7 is a section view of the third embodiment of the hiccup relieving apparatus as seen along line 7-7 of FIG. 6 in accordance with the present invention.

DESCRIPTION OF THE ENABLING EMBODIMENT

Figure 1:
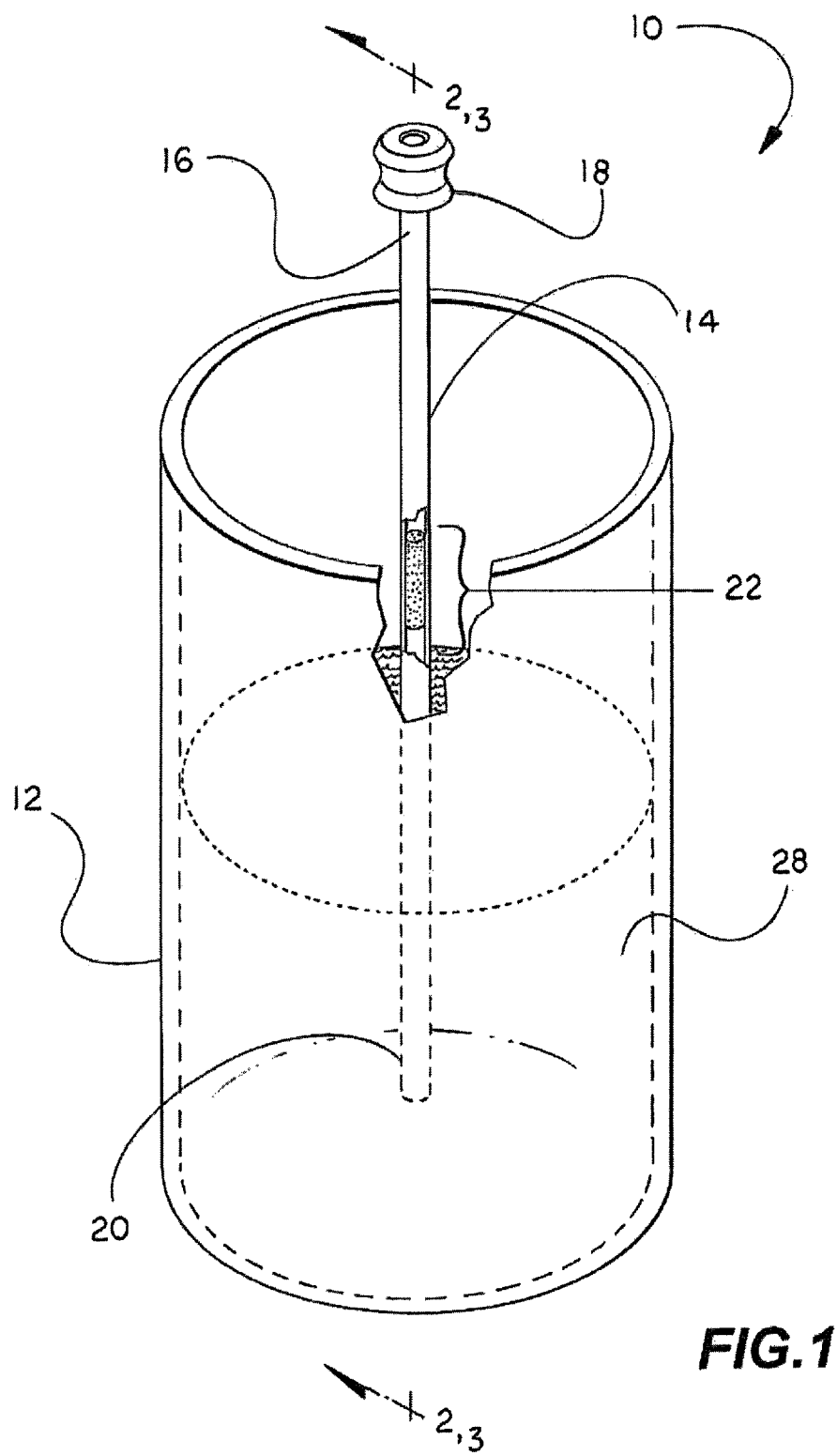
FIG. 1 is a perspective elevation view of a first embodiment of a hiccup relieving apparatus in accordance with the present invention.
Figure 2:
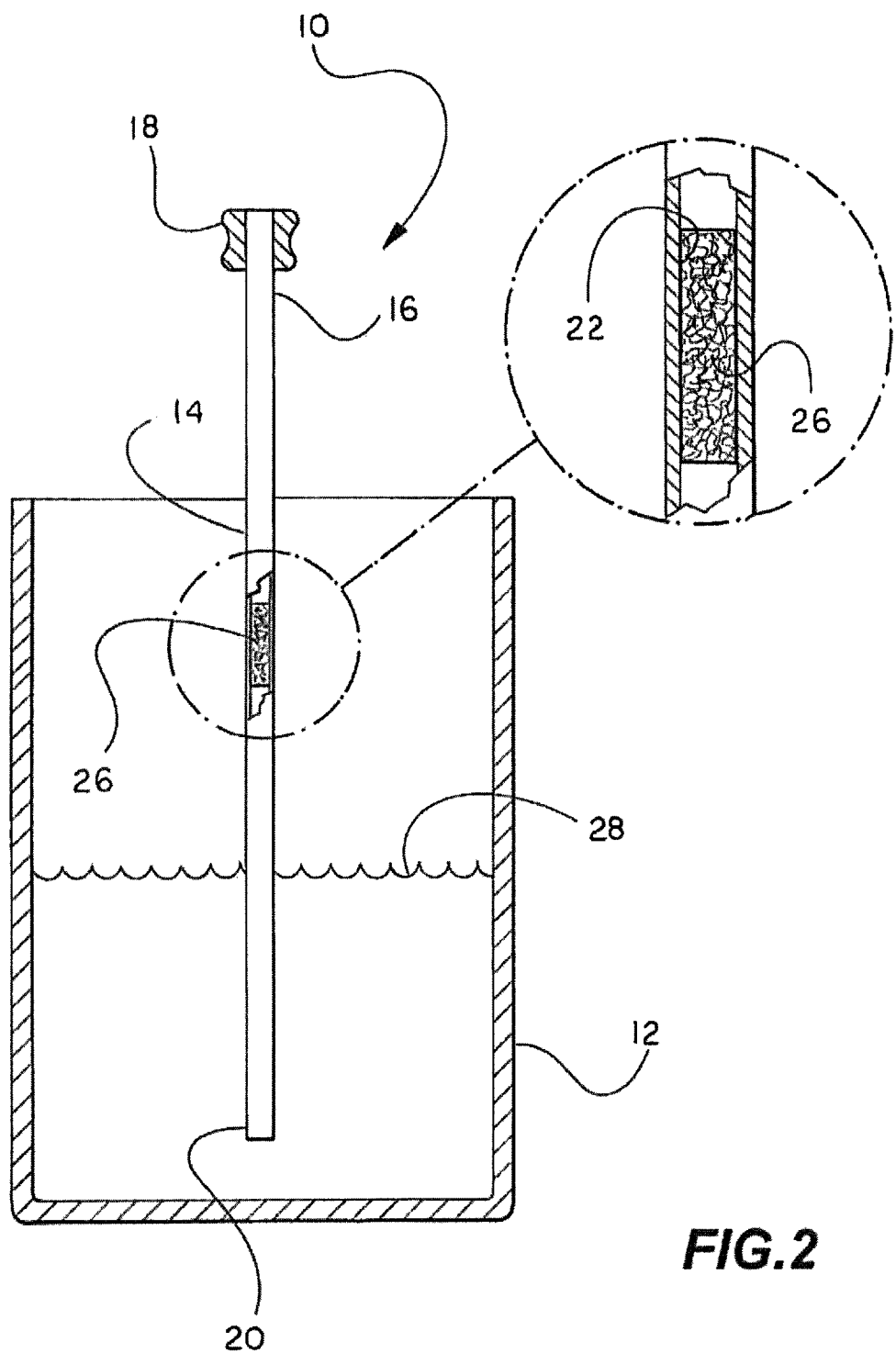
FIG. 2 is a section view of the first embodiment of the hiccup relieving apparatus along line 2-2 in FIG. 1 in accordance with the present invention.
Figure 3:
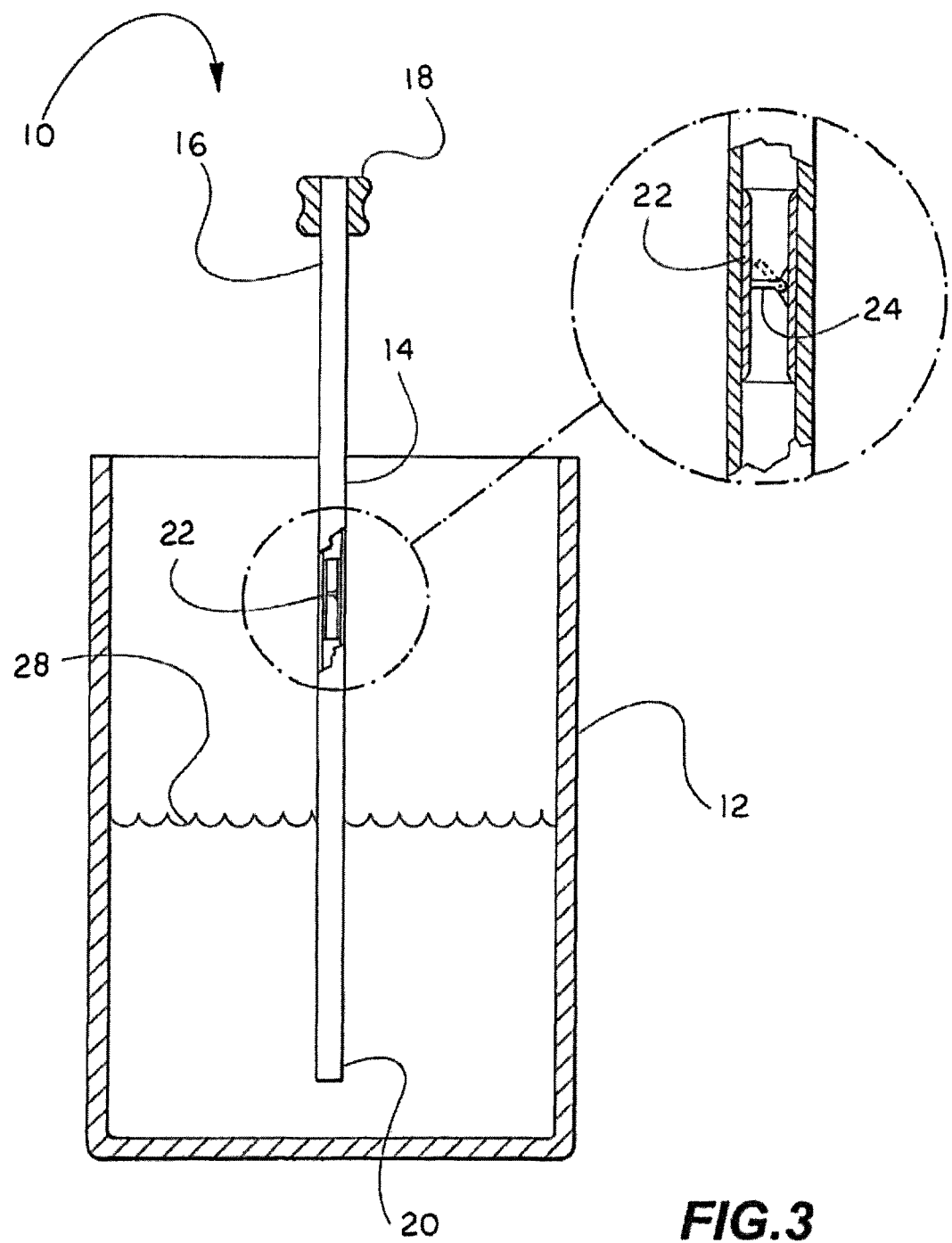
FIG. 3 is a section view of a second embodiment of the hiccup relieving apparatus along 10 the line 3-3 in FIG. 1 in accordance with the present invention.

Turning to FIGS. 1-3, a hiccup relieving apparatus 10 includes a tube 14 having a first end 16 and a second end 20. A mouthpiece 18, similar to a snorkel mouth piece, is attached to the first end 16, and the second end 20 is immersed in water or other potable liquid 28 in a container 12. The water or other potable liquid 28 in the container 12 is exposed to atmospheric pressure.

The tube 14 is approximately 1.5 to 2 cm in diameter. An obstruction 22 is positioned in the tube 14 between the first end 16 and the second end 20. The obstruction 22 is configured so that the user must apply suction to the mouthpiece 18 in order to produce a threshold suction of at least 20 cm of water for adults, and a section of at least 10 cm of water for children, before the water 28 in the water container 12 can be drawn through the tube 14 to the user. Target suction pressure is between 20 cm water and 40 cm of water for adults.

In a first embodiment of the present invention, the obstruction is a wad 26 of cotton or other cellulosic material. For an adult user, the cotton wad 26 is of sufficient size and density to require user suction of at least 20 cm of water before water or other potable liquid 28 will flow from the container 12 through the cotton wad 26 to the user. The requisite threshold suction of at least 20 cm of water can be created by a cylindrical cotton wad 26 having a diameter to fit inside the tube 14. By way of example, the cotton wad 26 could weigh approximately 5-10 grams. The tube 14 typically has a diameter of approximately 1.5 to 2 cm In one variation, the cotton wad 26 is rolled inside a paper towel so that the construction is similar to a cigarette filter. Typically, paper towels have a pore size of less than 100 microns.

In a second embodiment of the present invention, the obstruction 22 is a threshold valve 24. The threshold valve 24 is configured so that the threshold valve 24 opens when a threshold suction is applied to the threshold valve 24. The threshold suction useful for the hiccup relieving apparatus 10 is at least 20 cm of water for an adult user. Once the threshold suction produced by the user is reached, the threshold valve 24 opens and allows free flow of the water or other potable liquid 28 from the container 12 to the user through the tube 14. A threshold valve, such as threshold valve 24, is disclosed in Ratner U.S. Pat. No. 6,854,334, the disclosure of which is incorporated in its entirety by reference.

In a third embodiment of the present invention a hiccup relieving apparatus 110 is shown in FIGS. 4-7. The hiccup relieving apparatus 110 includes a tube 114 with a first end 116 and a second end 120. A mouthpiece 118 is molded to the first end 116. One or more orifices 130 are positioned at the second end 120. The second end 120 of the tube 114 of the hiccup relieving apparatus 110 is configured to be immersed in water or other potable liquid in a container. The water or other potable liquid in the container is exposed to atmospheric pressure. The three orifices 130 have diameters of 0.5 mm to 3 mm Particularly, the orifice diameters can be adjusted to control the amount of force required to suck the water or other potable liquid in the container into the user's mouth. Particular, the orifices are configured to assure that a suction of at least 20 cm of water is required for adult users.

The tube 114 is flat as shown in FIGS. 4 and 6. While the tube 114 could be circular, oval, or other configuration as well as the flat configuration, the flat configuration lends itself to molding the internal structure shown in FIG. 7. FIG. 7 shows two serpentine channels 132 that are connect to each other near the second end 120 and are connected the orifices 130. The two serpentine channels 32 are then connected to the mouthpiece 118. Water that is drawn by the user, enters through the orifices 130, pass through the serpentine channels 132 and is delivered to the user through the mouthpiece 118. The serpentine channels 132 are pressure breakers to prevent water from reaching the mouthpiece 118 too quickly.

A honeycomb structure 134 is positioned between the first end 116 and the second end 120 of the tube 114. The honeycomb structure 134 can be used to support an additional obstruction such as a cellulosic wad 26 or a threshold valve 24 as previously described. The honeycomb structure 134 therefore provides the options of the use of a cellulosic wad 26, a threshold valve 24, or no additional obstruction. In that way, the hiccup relieving apparatus 110 can be tuned to specific suction ranges with a combination of orifice size and/or specific obstruction.

Figure 10:
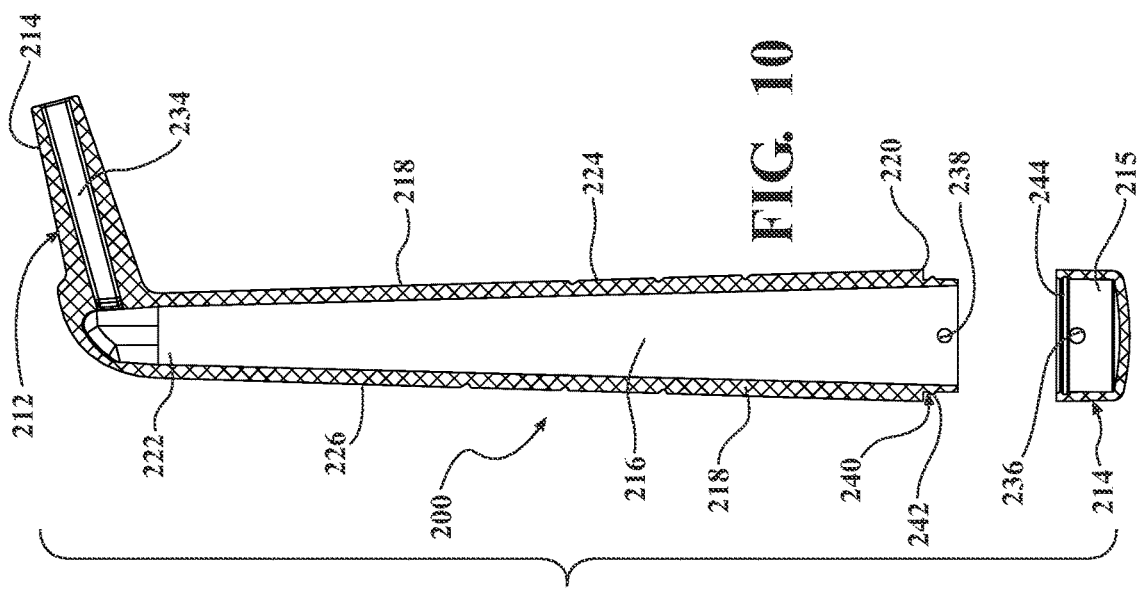
FIG. 10 is a cross sectional view of FIG. 9 taken along line A-A.
Figure 9:
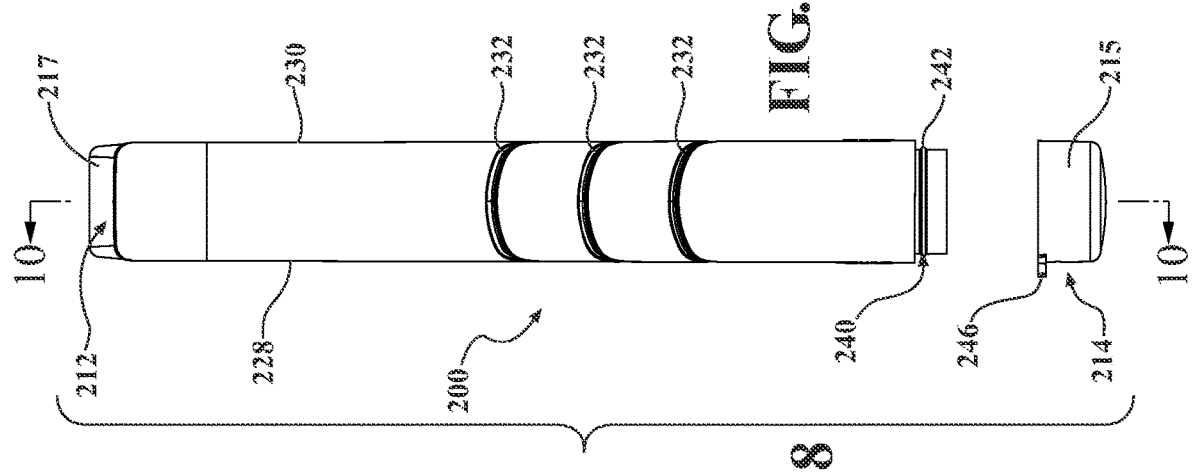
FIG. 9 is a back view of the fourth embodiment of the hiccup relieving apparatus of the present invention.
Figure 8:
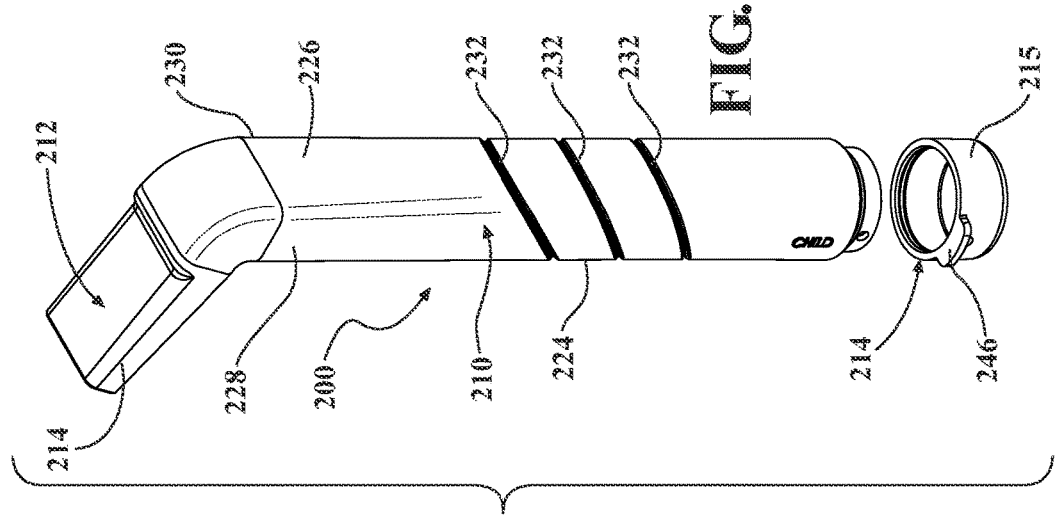
FIG. 8 is a perspective view of a fourth embodiment of the hiccup relieving apparatus of the present invention.

The fourth embodiment of the hiccup relieving apparatus is shown generally at 200 in FIGS. 8 through 10. The hiccup relieving apparatus 200 has a body portion 210, a mouth placement section 212 and a closed end 214.

Body portion 210 is illustrated as being generally tubular in shape defining an interior space or area 216. The walls 218 of body portion 210 are illustrated as converging walls with the interior 216 at the bottom 220 being wider than the interior 216 at the top 222. Also, as illustrated, the body portion 210 is generally rectangular in cross section, defining a front 224, a back 226, and opposed sides 228 and 230. The body 210 also has three grooves 232 formed in the exterior for aesthetic appeal. It will be appreciated by those of ordinary skill in the art of that the body portion 210 could have other shapes. The tubular shape for example could be straight or diverge from bottom 220 to top 222. The cross-section of the body portion 210 could also be for example square, hexagonal, octagonal, oval, or a combination of these, etc.

The mouthpiece section 212 of the present invention is illustrated as a mouthpiece 217 mounted to the top 222 of the body 210. As illustrated, the mouthpiece 217 is angled outwardly from the body 210 at approximately a 20° angle. This is considered a preferred angle for comfort and aesthetic appearance, however those of ordinary skill in the art will appreciate that other angles will work. For example, the mouthpiece could be at 90° or 180° angle with respect to the body 210, or any angle there between. As illustrated, the mouthpiece 217 is generally rectangular in cross-section, but could be any desired shape, such as square, oval, circular etc. The mouthpiece 217 has an orifice 234 in operative communication with the interior 216.

The closed end 214 of the illustrated embodiment is closed with a cap 215. It will be appreciated that other closures could be used, including but not limited to a unitary seal, a glued end, a threaded cap, a plug etc. The cap 215 is preferred because it allows for easy removal for cleaning and reattachment for use. The cap 215 attaches by snap fit to the bottom 220 of the body 210 in the illustrated embodiment. The cap 215 has two small holes 236 (only one is shown) that can be aligned with a hole 238 in the body 210, such that only one of the two holes is open at a given time. The holes 236 have different diameters, one for adults, which is smaller in diameter and one for children which is larger in diameter. It will be understood that further adjustments to flow could be obtained by adding more hole options in the endcap 215 or the body 210.

The cap 215 is illustrated as a snap fit connection. As illustrated, the body 210 has a narrower section 240 extending from the bottom 220 of body 210. A male retaining ring 242 protrudes from the section 240. The cap 215 has a female groove 244 that receives the ring 242. This allows the cap 215 to rotate with respect to the body 210. Timing notches or markings could also be provided to ensure proper alignment of holes 236 with hole 238.

The cap 215 is removable for cleaning. A tab 246 is provided to facilitate removal.

It should be appreciated by those of ordinary skill in the art that other closing methods could be used for closed end 214. For example, the closed end 214 could be sealed. In this event, the opening 238 would still be provided, it being understood that adjustability would not be available.

In use, a user suffering from hiccups places their mouth over the mouth placement section on the top 222 of the body 210. In the illustrated embodiment, the mouth placement section is a mouthpiece 217. The user then sucks on the mouthpiece 217 to draw fluid through the openings 236 and 238 into the interior space 216 and through the mouthpiece 217. The suction requires from 10 to 40 cm of water. The fluid could be air, water or other fluids. If it is air, the user just holds the body portion in their hand. With air only, the user must swallow saliva to engage the diaphragm and epiglottis muscles. If water is used, the user inserts the bottom end 220 into water so that the openings 236 and 238 are submerged. With water, the user swallows when the water is swallowed. As will be appreciated, the second opening is smaller than the first opening and the suction required to draw fluid through the small holes 236 and 238 into the interior 216 and through the mouthpiece 217 creates a pressure differential between the user's lungs and the atmospheric pressure to lower the user's diaphragm while simultaneously requiring the user to open and then close the user's epiglottis.

While this invention has been described with reference to preferred embodiments 15 thereof, it is to be understood that variations and modifications can be affected within the spirit and scope of the invention as described herein and as described in the appended claims.

What is claimed is:

1. A device configured for relieving hiccups comprising:
a body having a first end and a second end, said first and second ends being spaced from one another, wherein the body defines an interior space;
said first end having a first opening in fluid communication with said interior space and said second end having a first hole in communication with said interior space, said first opening configured to receive a user's mouth to draw liquid from a separate exterior source of liquid through said first hole into said interior space and through said first opening into the user's mouth, and wherein the liquid in the separate exterior source of liquid is exposed to atmospheric pressure;
said first hole is smaller than said first opening and is configured to create a pressure differential between the user's lungs and the atmospheric pressure when the user draws liquid through said first opening to lower the user's diaphragm while simultaneously requiring the user to open and then close the user's epiglottis, wherein the closing of the epiglottis prevents the liquid from entering the user's lungs;
a rotatable cover mounted on said second end covering said first hole, said cover having a second hole and a third hole, said second and third holes having different sizes, said rotatable cover being rotatable upon said second end to align either of said second and third holes with said first hole.

2. The device of claim 1, wherein said body is a hollow tube.

3. The device of claim 2, wherein said hollow tube has a rectangular cross section.

4. The device of claim 1, further including a mouthpiece connected to said first end in fluid communication with said first opening, and wherein the second and third holes at the second end are submerged in the liquid during use.

5. The device of claim 1, wherein the rotatable cover is a removeable cap.

6. The device of claim 1, wherein said first hole extends through said body portion.

7. The device of claim 1, wherein the first and second holes are sized to require a suction of at least 10 cm of the liquid.

8. The device of claim 1, wherein the first and third holes are sized to require a suction of at least 20 cm of the liquid.

9. The device of claim 1, wherein the rotatable cover is configured to enable only one of the second and third holes to be open at a given time.

10. The device of claim 9, wherein:
the second hole is open when aligned with the first hole; or
the third hole is open when aligned with the first hole.

11. The device of claim 1, wherein a different suction is required for drawing the liquid when the second hole is aligned with the first hole as compared to when the third hole is aligned with the first hole.

12. The device of claim 11, wherein the suction required is at least 20 cm of the liquid when one of the second or the third holes is aligned with the first hole.

13. The device of claim 1, wherein the second end comprising the second and third holes is submerged in the liquid during use.

14. A device configured for relieving hiccups comprising:
a body having a first end and a second end, said first and second ends being spaced from one another, wherein the body defines an interior space;
said first end having a first opening in fluid communication with said interior space and said second end having a first hole in communication with said interior space, said first opening configured to receive a user's mouth to draw liquid from a separate exterior source of liquid through said first hole into said interior space and through said first opening into the user's mouth, and wherein the liquid in the separate exterior source of liquid is exposed to atmospheric pressure;
said first hole is smaller than said first opening and is configured to create a pressure differential between the user's lungs and the atmospheric pressure when the user draws liquid through said first opening to lower the user's diaphragm while simultaneously requiring the user to open and then close the user's epiglottis;
a rotatable cover mounted on said second end covering said first hole, said cover having a second hole and a third hole, said second and third holes having different sizes, said rotatable cover being rotatable upon said second end to align either of said second and third holes with said first hole, and wherein the first hole and at least one of the second and third holes are sized to require a suction of at least 10 cm of the liquid.

15. The device of claim 14, wherein the rotatable cover is configured to enable only one of the second and third holes to be open at a given time.

16. The device of claim 15, wherein:
the second hole is open when aligned with the first hole; or
the third hole is open when aligned with the first hole.

17. The device of claim 14, wherein a different suction is required for drawing the liquid when the second hole is aligned with the first hole as compared to when the third hole is aligned with the first hole.

18. The device of claim 17, wherein the suction required is at least 20 cm of the liquid when one of the second or the third holes is aligned with the first hole.

19. The device of claim 14, wherein the second end comprising the second and third holes is submerged in the liquid during use.

* * * * *